(12) United States Patent
Arba Mosquera

(10) Patent No.: US 12,383,430 B2
(45) Date of Patent: Aug. 12, 2025

(54) METHOD FOR PROVIDING CONTROL DATA FOR AN EYE SURGICAL LASER OF A TREATMENT APPARATUS

(71) Applicant: SCHWIND eye-tech-solutions GmbH, Kleinostheim (DE)

(72) Inventor: Samuel Arba Mosquera, Aschaffenburg (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 86 days.

(21) Appl. No.: 17/325,623

(22) Filed: May 20, 2021

(65) Prior Publication Data

US 2021/0361486 A1    Nov. 25, 2021

(30) Foreign Application Priority Data

May 22, 2020   (DE) .................... 10 2020 113 820.2

(51) Int. Cl.
| | | |
|---|---|---|
| A61F 9/008 | (2006.01) | |
| A61F 9/009 | (2006.01) | |
| A61B 18/00 | (2006.01) | |

(52) U.S. Cl.
CPC .......... *A61F 9/00827* (2013.01); *A61F 9/009* (2013.01); *A61B 2018/00726* (2013.01);
(Continued)

(58) Field of Classification Search
CPC ................. A61F 9/00827; A61F 9/009; A61B 2018/00726; A61B 2018/00761; A61B 2018/00878

See application file for complete search history.

(56) References Cited

U.S. PATENT DOCUMENTS

| | | | |
|---|---|---|---|
| 7,237,898 B1 * | 7/2007 | Hohla | ............... G06V 40/18 606/5 |
| 2011/0034911 A1 | 2/2011 | Bischoff et al. | |

(Continued)

FOREIGN PATENT DOCUMENTS

| | | |
|---|---|---|
| DE | 102006053120 A1 | 5/2008 |
| DE | 102008017293 A1 | 10/2009 |

OTHER PUBLICATIONS

Chang, A. W., Tsang, A. C., Contreras, J. E., Huynh, P. D., Calvano, C. J., Crnic-Rein, T. C., Thall, E. H. (2003). Corneal tissue ablation depth and the Munnerlyn formula. Journal of Cataract and Refractive Surgery, 29(6), 1204-1210. https://doi.org/10.1016/s0886-3350(02)01918-1 (Year: 2003).*

(Continued)

*Primary Examiner* — Lynsey C Eiseman
*Assistant Examiner* — Skylar Lindsey Christianson
(74) *Attorney, Agent, or Firm* — MEDLER FERRO WOODHOUSE & MILLS PLLC

(57) ABSTRACT

A method for providing control data of an eye surgical laser is disclosed. A control device ascertains a lenticule geometry of the lenticule to be separated from predetermined visual disorder data of a human or animal eye. The lenticule geometry is defined by means of a refractive power value to be corrected and a lenticule diameter. The control device ascertains a correction value for compensating for a deformation of the lenticule, which is generated by at least one contact element of the treatment apparatus. The control device ascertains a deformation geometry of the lenticule, wherein the deformation geometry is defined by means of the refractive power value and a deformation diameter. The deformation diameter is calculated depending on the lenticule diameter and the correction value, and provides control (Continued)

data for controlling the eye surgical laser, which uses the deformation geometry for the separation of the lenticule.

12 Claims, 2 Drawing Sheets

(52) U.S. Cl.
CPC ............... *A61B 2018/00761* (2013.01); *A61F 2009/00878* (2013.01)

(56) References Cited

U.S. PATENT DOCUMENTS

| | | | |
|---|---|---|---|
| 2016/0150952 A1* | 6/2016 | Raymond | ........... A61F 9/00829 351/205 |
| 2018/0153741 A1 | 6/2018 | Dai et al. | |
| 2019/0247225 A1* | 8/2019 | Stobrawa | ............ A61F 9/00836 |

OTHER PUBLICATIONS

Extended European Search Report issued Sep. 27, 2021 in corresponding European Patent Application No. 21175004.7.

\* cited by examiner

METHOD FOR PROVIDING CONTROL DATA FOR AN EYE SURGICAL LASER OF A TREATMENT APPARATUS

The present device relates to a method for providing control data for an eye surgical laser of a treatment apparatus for the separation of a lenticule. In addition, the invention relates to a treatment apparatus with at least one eye surgical laser and at least one control device for performing the method, to a computer program and to a computer-readable medium.

Treatment apparatuses and methods for controlling ophthalmological lasers for correcting an optical visual disorder are known in the prior art. Therein, a pulsed laser and a beam focusing device can for example be formed such that laser beam pulses effect a photodisruption in a focus located within the organic material to separate a lenticule from the cornea for correcting the visual disorder. In the treatment with a treatment apparatus for separating a lenticule, the eye is usually fixed by one or more contact elements of the treatment apparatus. Herein, the contact element is a rigid element, for example a plano-concave lens, which is fitted onto the eye, in particular onto the cornea, in order that the eye is not moved in the treatment. However, it is disadvantageous with such a contact element that a shape of the cornea cannot be exactly adapted to the contact element, whereby the cornea deforms by the contact element. Hereby, the shape of the lenticule to be separated can also change, whereby a treatment, in particular an achieved refractive power value, can be defective. In order to compensate for this, a user of the treatment apparatus, for example a physician, can adapt a refractive power value to be corrected in planning the treatment according to its experiences, such that the achieved refractive power value matches the correction of the optical visual disorder despite of the contact element. However, despite of the matching refractive power, an achieved lenticule height can deviate from a planned lenticule height, whereby more tissue than necessary can for example be removed from the cornea.

The invention is based on the object to provide control data for controlling an eye surgical laser, in which a compensation for a deformation of a lenticule, which is generated by a contact element, is provided in simple manner.

This object is solved by the method according to the invention, the apparatuses according to the invention, the computer program according to the invention as well as the computer-readable medium according to the invention. Advantageous configurations with convenient developments of the invention are specified in the respective dependent claims, wherein advantageous configurations of the method are to be regarded as advantageous configurations of the treatment apparatus, of the control device, of the computer program and of the computer-readable medium and vice versa.

A first aspect of the invention relates to a method for providing control data of an eye surgical laser of a treatment apparatus for the separation of a lenticule, wherein the method comprises the following steps performed by a control device. Therein, an appliance, an appliance component or an appliance group is understood by a control device, which is configured for receiving and evaluating signals as well as for providing, for example generating, control data. The control device can for example be configured as a control chip, computer program, computer program product or control appliance. Ascertaining a lenticule geometry of the lenticule to be separated, which includes a lenticule height, from predetermined visual disorder data of a human or animal eye, wherein the lenticule geometry is defined by means of a refractive power value to be corrected and a lenticule diameter, and ascertaining a correction value for compensating for a deformation of the lenticule, which is generated by at least one contact element of the treatment apparatus, wherein the correction value is determined by means of at least one preceding measurement of the treatment apparatus, are effected by the control device. Further, ascertaining a deformation geometry of the lenticule, which includes a deformation height, is effected by the control device, wherein the deformation geometry is defined by means of the refractive power value and a deformation diameter, wherein the deformation diameter is calculated depending on the lenticule diameter and the correction value. Finally, providing control data for controlling the eye surgical laser is effected by the control device, wherein the control data uses the deformation geometry for separating the lenticule.

In other words, the lenticule geometry of the lenticule to be separated is first determined from previously determined visual disorder data. The visual disorder data can for example describe ametropia, thus deviation of the refractive power of an eye or a cornea from the ideal value, for example myopia, hyperopia or astigmatism. For example, the visual disorder data can describe a value of a refractive power, thus an indication in diopters, or for example a deviation of a corneal curvature from a normal value. For example, the visual disorder data can be effected by retrieving the visual disorder data from a data storage or data server, or the visual disorder data can for example be received from a measuring appliance performing measurements of the cornea and/or determining the ametropia. Based on the determined visual disorder data, the control device ascertains a lenticule geometry, which describes the dimensions of a lenticule and the position thereof in the cornea. That is, the lenticule geometry, thus the desired shape of the lenticule and the position thereof in the cornea, is determined by means of the visual disorder data, wherein a lenticule height is in particular defined by means of a refractive power value to be corrected and a lenticule diameter, which is also called optical zone. Therein, a volume body of the cornea is understood by a lenticule, thus for example a discus-shaped disc, which can be defined by anterior and posterior interfaces. For example, the interfaces can form a biconvex, biconcave, concavo-convex, convexo-concave, plane parallel, plano-convex or plano-concave volume body.

After or before this method step, the control device can ascertain a correction value for compensating for a deformation of the lenticule, wherein the deformation of the lenticule is generated by the contact element of the treatment apparatus. Herein, the correction value is determined from at least one preceding measurement by the treatment apparatus. That is, the correction value is empirically determined, from a previously performed measurement with the treatment apparatus.

By means of the correction value, a deformation geometry of the lenticule can then be ascertained, wherein hereto a deformation diameter is determined from the lenticule diameter and the correction value, by means of which the lenticule height to be corrected is achieved. Then, the deformation geometry can be determined from the refractive power value and the deformation diameter, which in particular describes the shape of the lenticule, which is to be used for compensation for the deformation by the at least one contact element of the treatment apparatus. Finally, the control data can be provided for controlling the eye surgical laser, which uses the deformation geometry for separating the lenticule instead of the lenticule geometry.

By this aspect of the invention, the advantage arises that treatment results can be further improved, in particular a height to be separated of the lenticule can be correctly determined to compensate for deformation effects due to a contact element, wherein a manual adaptation of the refractive power value to be corrected can for example be previously performed hereto. This means that for example a physician can adapt the refractive power value before the treatment due to its experience for compensating for the deformation by the contact element as usual and a deformation geometry of the lenticule adapted thereto is additionally determined by the method according to the invention, by which an amount of tissue to be removed from the cornea is optimized.

According to an advantageous form of configuration, it is provided that the correction value is ascertained from a deviation of the lenticule height, which is expected according to the lenticule geometry, and an achieved lenticule height, wherein the achieved lenticule height is determined after application of the treatment apparatus without use of the deformation geometry. In other words, the deviation can be determined, which is present between the expected lenticule height, that is the planned lenticule height, and the achieved lenticule height, if the deformation geometry is not used.

The correction value can then be determined from it. For example, it can have been planned from the lenticule geometry that a lenticule height of 100 micrometers is separated in the treatment, wherein the maximum height of the lenticule is here meant by lenticule height. However, due to the deformation of the lenticule, a lenticule height of 107 micrometers can for example be separated, wherein the refractive power value previously can have been manually adapted. This would result in a deviation of 7 percent, wherein the correction value is preferably ascertained such that these 7 percent of deviation are compensated for. In order to determine this deviation between the lenticule heights, the measurement without use of the deformation geometry can preferably be performed on artificial corneas and/or on animal corneas and/or on human donor corneas. By this form of configuration, the advantage arises that the correction value can be determined by means of a simple measurement.

It is advantageous if the correction value is statistically determined from multiple preceding measurements of the lenticule height and the achieved lenticule height, in particular by means of a linear regression. This has the advantage that the correction value becomes more robust with respect to statistical deviations. For example, multiple measurements can be performed, for example for multiple planned lenticule heights between 40 and 120 micrometers, which are each compared to the achieved lenticule heights. Hereto, known statistical methods can be applied, in particular a linear regression, the slope of which can represent the deviation between the lenticule heights.

It is further advantageous if the achieved lenticule height is determined at least at two different points of time, wherein the correction value is ascertained from an average value of the deviations at the at least two different points of time. In particular, one of the points of time can be shortly after the treatment, for example one day or one week after the treatment, and the other point of time can be later, for example after one month. The achieved lenticule height at these two or also more points of time can then be averaged to determine the deviation from the lenticule height to be expected, wherefrom the correction value can then be determined. This has the advantage that the correction value becomes statistically more robust by the use of multiple measurements.

According to a further advantageous form of configuration, it is provided that the correction value is combined with a refractive power correction value, wherein the refractive power correction value is ascertained from a deviation of the refractive power value to be corrected and an achieved refractive power value, in particular by means of a linear regression from multiple preceding measurements and an average value from refractive power deviations at different points of time, wherein the achieved refractive power value is determined after an application of the treatment apparatus. In other words, the correction value, which is ascertained from a deviation of the expected and the achieved lenticule height, can be combined with a refractive power correction value, wherein the refractive power correction value is ascertained from a deviation of the planned and the achieved refractive power value. Therein, the refractive power correction value can preferably be determined by means of the same statistical approaches as the correction value. By this form of configuration, the advantage arises that a deviation of the refractive power value can be additionally taken into account in ascertaining the deformation geometry. Due to the deformation of the lenticule by the contact element, it is for example provided that the physician correspondingly adapts the refractive power value from empirical values to achieve a compensation for the deformation. However, this adaptation of the refractive power value cannot be optimum and a deviation from the refractive power value to be corrected to the achieved refractive power value can still be present, which can be determined from measurements with the treatment apparatus. In order to additionally compensate for this deviation of the refractive power values, therefore, the refractive power correction value can be combined with the correction value in that the correction value is for example multiplied by the reciprocal value of the refractive power correction value. For example, the refractive power values can have a 7 percent deviation from each other on average, wherein these 7 percent can then be the refractive power correction value, which is combined with the correction value.

Preferably, the correction value is in a range from 0.7 to 1.5, in particular in a range from 1.0 to 1.4. That is, if a deviation of 10 percent has been determined between the lenticule height, which is expected from the lenticule geometry, and the ascertained lenticule height, the correction value can be at 1.1. Together with the above mentioned refractive power correction value, this would result in an overall correction value of about 1.18.

According to a further advantageous form of configuration, the deformation diameter is calculated by means of a multiplication of the lenticule diameter by a parameter depending on the correction value, wherein the parameter is determined by means of a theoretical lenticule geometry model, in particular by means of the Munnerlyn formula. In other words, the deformation diameter can be calculated from the lenticule diameter, that is the planned lenticule diameter, for calculating the deformation geometry in that the lenticule diameter is multiplied by a parameter, wherein the parameter is dependent on the correction value. It is meant by the parameter depending on the correction value that it includes a mathematical calculation operation with the correction value, in particular a power of the correction value. In particular, the parameter depending on the correction value can be determined from a lenticule geometry model, preferably from the lenticule geometry model, by which the lenticule geometry is ascertained, for example by means of the Munnerlyn formula.

According to a further advantageous form of configuration, a height is ascertained for the deformation height of the deformation geometry, which corresponds to a multiplication of the lenticule height by the reciprocal value of the correction value, in that the deformation diameter is calculated by means of a division of the lenticule diameter by the square root of the correction value.

In other words, the deformation height reduces to a height, which corresponds to the lenticule height divided by the correction value. Thereto, the deformation diameter is calculated by means of a division of the lenticule diameter by the "correction value to the power of ½". Therein, the square root of the correction value is in particular obtained from an analytical calculation of the lenticule geometry model, preferably from a calculation by means of the Munnerlyn formula.

A second aspect of the present invention relates to a control device, which is configured to perform one of the above described methods. The above cited advantages arise. The control device can for example be configured as a control chip, control appliance or application program ("app"). Preferably, the control device can comprise a processor device and/or a data storage. An appliance or an appliance component for electronic data processing is understood by a processor device. For example, the processor device can comprise at least one microcontroller and/or at least one microprocessor. Preferably, a program code for performing the method according to the invention can be stored on the optional data storage. The program code can be configured to cause the control device to perform one of the above described embodiments of one or both methods according to the invention upon execution by the processor device.

A third aspect of the present invention relates to a treatment apparatus with at least one eye surgical laser for the separation of a predefined corneal volume with predefined interfaces of a human or animal eye by means of photodisruption, and at least one control device for the laser or lasers, which is formed to execute the steps of the method according to the first aspect of the invention. The treatment apparatus according to the invention allows that the disadvantages occurring in the use of usual ablative treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for producing volume bodies within the cornea. The use of photodisruptive lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is allowed. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the control dataset or datasets include control data for positioning and/or for focusing individual laser pulses in the cornea, and can comprise at least one beam device for beam guidance and/or beam shaping and/or beam deflection and/or beam focusing of a laser beam of the laser. Therein, the mentioned control datasets are usually generated based on a measured topography and/or pachymetry and/or morphology of the cornea to be treated and the type of the visual disorder to be corrected.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including instructions, which cause the treatment apparatus according to the third inventive aspect to execute the method steps according to the first inventive aspect and/or the method steps according to the second inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

Figure 1:
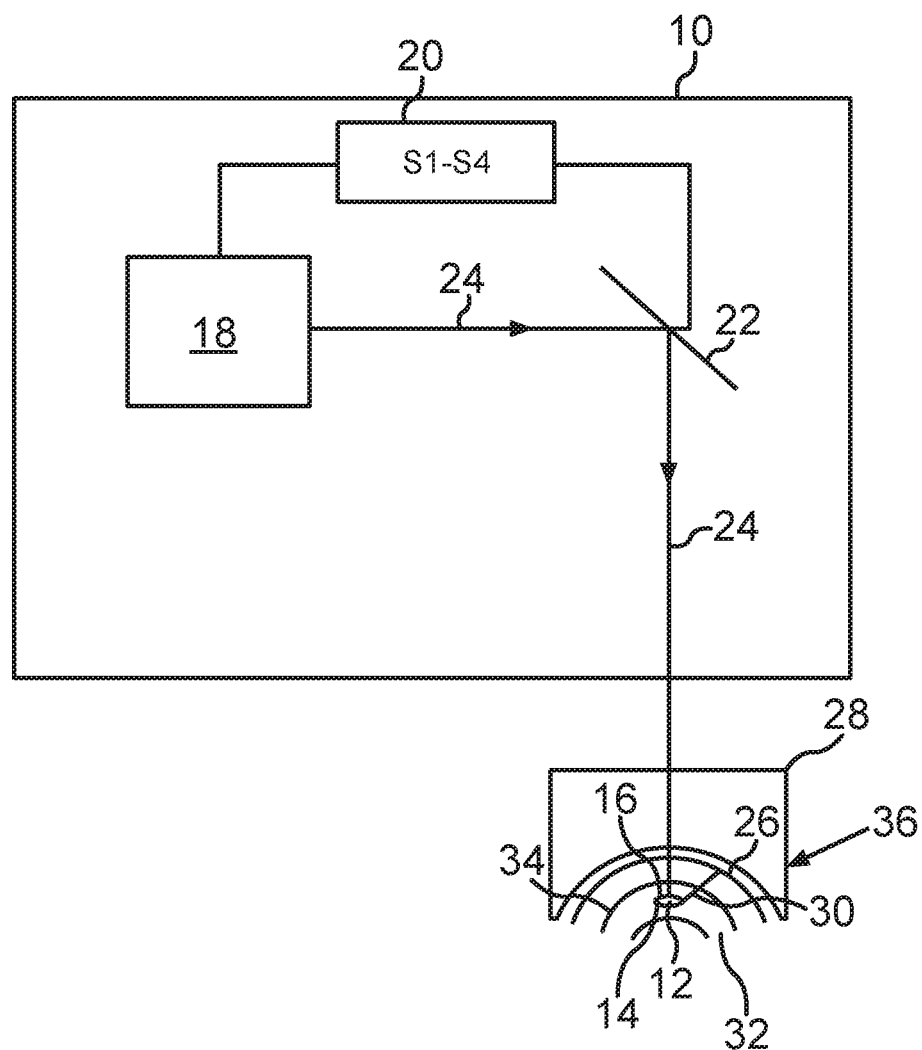
FIG. 1 shows a schematic representation of a treatment apparatus according to the invention according to an exemplary embodiment.

FIG. 1 shows a schematic representation of a treatment apparatus 10 with an eye surgical laser 18 for the separation of a corneal volume/cornea volume predefined by a lenticule geometry of a cornea of a human or animal eye 36, thus a lenticule 12, which can also be referred to as volume body, with predefined interfaces 14, 16 by means of photodisruption. One recognizes that a control device 20 for the laser 18 can be formed besides the laser 18 such that it emits pulsed laser pulses for example in a predefined pattern into the cornea of the eye 36, wherein the ascertained interfaces 14, 16 of the lenticule 12 to be formed can for example be generated by a predefined pattern by means of photodisruption. Alternatively, the control device 20 can be a control device 20 external with respect to the treatment apparatus 10.

The ascertained interfaces 14, 16 form a lenticule 12 in the illustrated embodiment, wherein the position of the lenticule 12 is selected in this embodiment such that it can for example be located within a stroma 32 of the cornea. Furthermore, it is apparent from FIG. 1 that the so-called Bowman's membrane 34 can be formed between the stroma 32 and an epithelium.

Furthermore, FIG. 1 shows that the laser beam 24 generated by the laser 18 is deflected towards a surface 26 of the cornea by means of a beam device 22, namely a beam deflection device, such as for example a rotation scanner. The beam deflection device is also controlled by the control device 20 to generate the ascertained interfaces 14, 16, preferably also incisions or cuts 30, along preset incision progressions.

Preferably, the illustrated laser 18 can be a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz. Additionally, the control device 20 optionally comprises a storage device (not illustrated) for at least temporary storage of at least one control dataset, wherein the control dataset or datasets include control data for positioning and/or for focusing individual laser pulses in the cornea. The position data and/or focusing data of the individual laser pulses, that is the lenticule geometry of the lenticule 12 to be separated, are generated based on predetermined visual disorder data, in particular from a previously measured topography and/or pachymetry and/or the morphology of the cornea or the optical visual disorder correction to be generated exemplarily within the stroma 32 of the eye 36. For determining the visual disorder data, which can for example indicate a value in diopters, or other suitable data for describing the visual disorder, the control device 20 can for example receive the corresponding data from a data server or the visual disorder data can be determined as a data input. The lenticule geometry of the lenticule 12 to be separated for correcting the visual disorder includes a lenticule height and is in particular defined by means of a refractive power value to be corrected, which can also be referred to as planned refractive power value, and a lenticule diameter, which is also referred to as optical zone. The lenticule height or also lenticule thickness is a variable value, which indicates the height of the lenticule in an anterior-posterior direction, that is parallel to an optical axis of the eye 36, depending on a position perpendicular to the optical axis, in particular depending on a position in a radial direction of the lenticule. An exact progression of the lenticule height depending on the position in radial direction can for example be determined by means of a theoretical lenticule geometry model, in particular by means of the Munnerlyn formula.

Further, a contact element 28 can be provided, which can be associated with the treatment apparatus 10. Alternatively, the contact element 28 can also be provided separately from the treatment apparatus 10. The contact element 28, which can be referred to as patient interface or fixing system, serves to fix the eye 36 for the treatment. Hereto, the contact element 28 can comprise a plano-concave lens, which is adapted to the eye 36 for fixing. By fixing by means of the contact element 28, however, it can occur that the cornea deforms and thus the ascertained lenticule geometry for separating the lenticule 12 does no longer optimally apply to the predetermined visual disorder data. Therefore, it can occur that a planned lenticule height or lenticule height to be corrected deviates from an achieved lenticule height after the treatment with the treatment apparatus 10.

Such a deviation, which arises by the contact element 28, can be known to a user of the treatment apparatus 10, in particular to a physician. Therefore, the physician will preferably adapt the refractive power value to be corrected in the planning according to his empirical values, for example by increasing the refractive power value, such that the achieved refractive power value corresponds to the desired correction after the treatment with the treatment apparatus.

Figure 2:
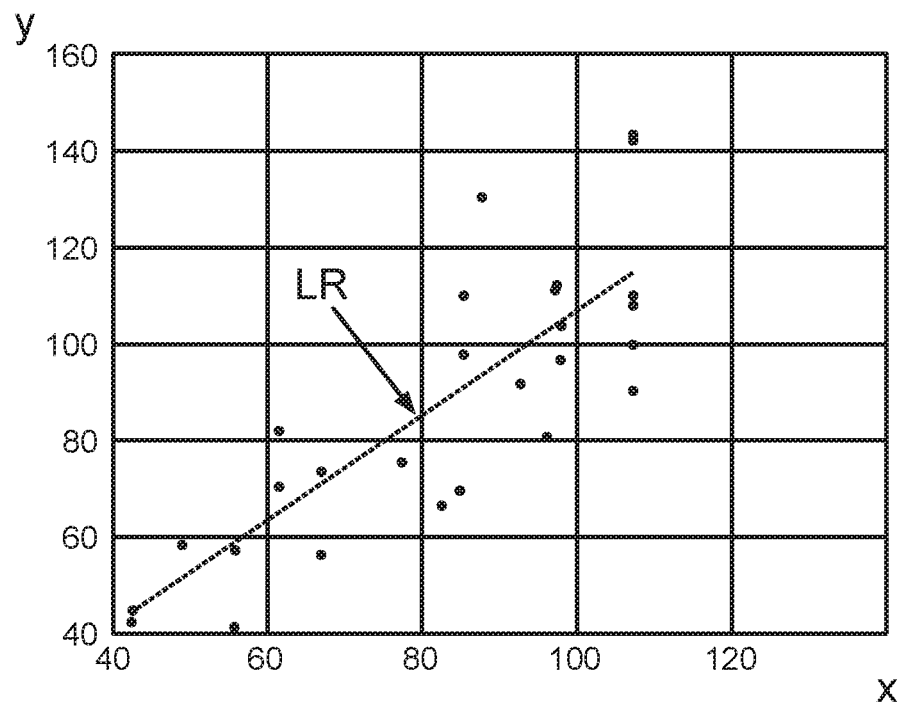
FIG. 2 shows an exemplary scatter plot of expected and achieved lenticule heights.

The deformation by the contact element 28 can result in the fact that the removed lenticule height is not optimum. For example, an achieved lenticule height can be larger than required or planned. That is, more tissue would have been removed from the cornea than required. For example, this is presented in the scatter plot of FIG. 2. In FIG. 2, the lenticule height (in micrometers) is plotted on the x-axis, which is expected by the treatment, and the achieved lenticule height (in micrometers) one day after the treatment is plotted on the y-axis. In this example, a linear regression line LR can have a slope of 1.07.

Figure 3:
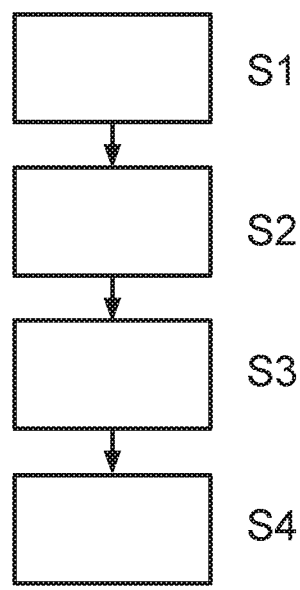
FIG. 3 shows a schematic method diagram according to an exemplary embodiment.

In order to compensate for this deviation, it can be provided that the control device 20 performs the method steps S1 to S4 described below, which are for example presented as a method diagram in FIG. 3. In step S1, as described above, the lenticule geometry of the lenticule 12 to be separated is determined from the predetermined visual disorder data, wherein the lenticule geometry is defined by means of the refractive power value to be corrected and the lenticule diameter. Therein, the refractive power value to be corrected can be adapted according to empirical values from the physician. Subsequently, a correction value for compensating for the deformation by the contact element 28 can be determined from at least one preceding measurement with the treatment apparatus 10 in step S2. Preferably, the correction value can be statistically determined from the measurements of FIG. 2 in that the slope of the regression line LR is used as the correction value, thus 1.07 in the above example.

However, the previously shown numbers are only to represent examples of the correction value and the correction value can for example be different according to treatment apparatus and associated contact element. A type of the treatment, that is depending on the visual disorder data, and an adaptation of the refractive power value by the physician can also change the correction value. In particular, the correction value can be in a range from 0.7 to 1.5, preferably in a range from 1.0 to 1.4.

After ascertaining the correction value, a deformation geometry of the lenticule 12 can be ascertained by the control device in step S3, wherein the refractive power value of the lenticule geometry, in particular the refractive power value, which was set by the physician, can be adopted for the deformation geometry. The lenticule diameter can be divided by a parameter depending on the correction value as a deformation diameter of the deformation geometry, wherein the parameter is determined by means of a theoretical lenticule geometry model. For example, the lenticule geometry model can be that model, by means of which the lenticule geometry was previously determined. Preferably, the lenticule geometry model can be the Munnerlyn formula, wherein the parameter depending on the correction value is therein the square root of the correction value. This means that the deformation diameter is calculated in that the lenticule diameter is divided by the square root of the correction value, thus by the root of 1.07 in the above example. Accordingly, a deformation height is ascertained by means of the deformation geometry, which corresponds to the lenticule height divided by the correction value.

The deformation geometry thus determined can then be provided in the form of control data for controlling the eye surgical laser 18 by the control device 20 in a step S4. By means of the thus provided control data, which uses the deformation geometry for separating the lenticule 12, a compensation for the deformation by the contact element 28 can be achieved in simple manner, wherein a height of the lenticule 12 to be separated can be kept small. Hereby, a treatment with the treatment apparatus 10 can be improved.

What is claimed is:

1. A method for providing control data for an eye surgical laser of a treatment apparatus for separation of a lenticule, wherein the method comprises the following steps performed by a control device:
    ascertaining a lenticule geometry of the lenticule to be separated, which includes a lenticule height, from predetermined visual disorder data of a human or animal eye, wherein the lenticule geometry is defined by means of a refractive power value to be corrected and a lenticule diameter;
    ascertaining a correction value for compensating for a deformation of the lenticule, which is generated by at least one contact element of the treatment apparatus, wherein the correction value is determined empirically from at least one measurement compensating for deformation of a lenticule of a preceding eye treatment of another eye that was treated with the treatment apparatus without the use of the correction value;
    ascertaining a deformation geometry of the lenticule, which includes a deformation height, wherein the deformation geometry is defined by means of the refractive power value and a deformation diameter, wherein the deformation diameter is calculated depending on the lenticule diameter and the correction value; and
    providing control data for controlling the eye surgical laser, which uses the deformation geometry for separating the lenticule;
    wherein the correction value is ascertained from a deviation of the lenticule height, which is expected according to the lenticule geometry, and an achieved lenticule height, wherein the achieved lenticule height is determined after an application of the treatment apparatus without the use of the deformation geometry; and
    wherein the achieved lenticule height is measured at least at two different points of time, wherein the correction value is ascertained from an average value of deviations between the at least two different points of time.

2. The method according to claim 1, wherein the correction value is statistically determined from multiple preceding measurements of the lenticule height and the achieved lenticule height, in particular by means of a linear regression.

3. The method according to claim 1, wherein
    the correction value is combined with a refractive power correction value,
    the refractive power correction value is ascertained from a deviation of the refractive power value to be corrected and an achieved refractive power value, in particular by means of a linear regression from multiple preceding measurements and an average value from refractive power value deviations at different points of time, and
    the achieved refractive power value is determined after the application of the treatment apparatus.

4. The method according to claim 1, wherein the correction value is in a range from 0.7 to 1.5.

5. The method according to claim 1, wherein the deformation diameter is calculated by means of a multiplication of the lenticule diameter by a parameter depending on the correction value, and wherein the parameter is determined by means of a theoretical lenticule geometry model.

6. The method according to claim 5, wherein a height is ascertained for the deformation height of the deformation geometry, which corresponds to a multiplication of the lenticule height by a reciprocal value of the correction value, in that the deformation diameter is calculated by means of a division of the lenticule diameter by a square root of the correction value.

7. A control device, which is formed to perform the method according claim 1.

8. A treatment apparatus with at least one eye surgical laser for the separation of a lenticule of a human or animal eye by means of photodisruption and at least one control device according to claim 7.

9. The treatment apparatus according to claim 8, wherein the eye surgical laser is formed to emit laser pulses in a wavelength range between 300 nm and 1400 nm, at a respective pulse duration between 1 fs and 1 ns, and a repetition frequency of greater than 10 kHz.

10. The treatment apparatus according to claim 9, wherein the eye surgical laser is formed to emit laser pulses in a wavelength range between 700 nm and 1200 nm, at a respective pulse duration between 10 fs and 10 ps, and a repetition frequency of between 100 kHz and 100 MHz.

11. The treatment apparatus according to claim 8, wherein the control device comprises at least one storage device for at least temporary storage of at least one control dataset, wherein the at least one control dataset includes control data for positioning and/or focusing individual laser pulses in the human or animal eye; and
    includes at least one beam device for beam guidance and/or beam shaping and/or beam deflection and/or beam focusing of a laser beam of the eye surgical laser.

12. A non-transitory computer-readable medium having stored thereon a computer program, the computer program including instructions, which cause a treatment apparatus with at least one eye surgical laser for the separation of a lenticule of a human or animal eye by means of photodisruption, and at least one control device to execute the method according to claim 1.

* * * * *